US00PP35193P2

(12) United States Plant Patent
Miyazaki

(10) Patent No.: US PP35,193 P2
(45) Date of Patent: May 23, 2023

(54) ***SENECIO* PLANT NAMED 'SENE NIRENAGO'**

(50) Latin Name: *Senecio cruentus*
Varietal Denomination: Sene Nirenago

(71) Applicant: Kiyoshi Miyazaki, Shiga (JP)

(72) Inventor: Kiyoshi Miyazaki, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 17/967,662

(22) Filed: Oct. 17, 2022

(51) Int. Cl.
*A01H 5/02* (2018.01)
*A01H 6/14* (2018.01)

(52) U.S. Cl.
USPC ..... Plt./480
CPC ..... *A01H 6/14* (2018.05)

(58) Field of Classification Search
USPC ..... Plt./480
CPC ..... A01H 6/14; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Senecio* plant named 'Sene Nirenago', characterized by its upright and uniformly mounded plant habit; vigorous growth habit; freely branching habit; freely flowering habit; and daisy-type inflorescences with ray florets that are deep violet and light reddish purple in color.

1 Drawing Sheet

Figure 1:
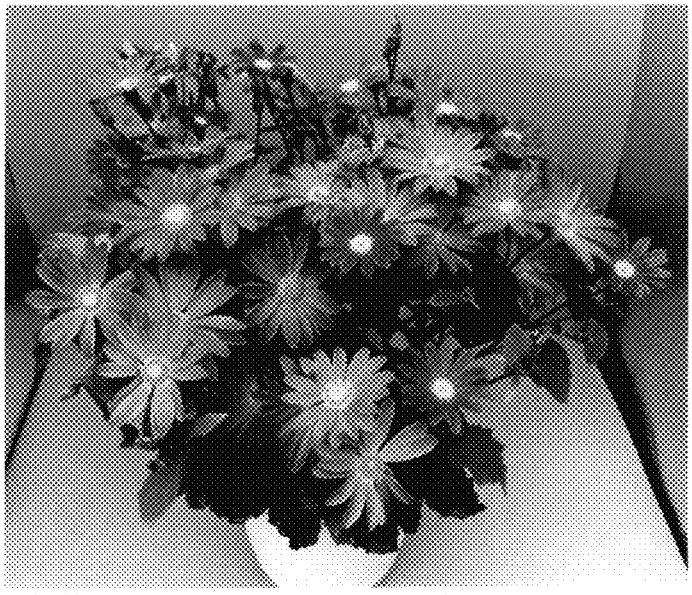

Botanical designation: *Senecio cruentus.*
Cultivar denomination: 'SENE NIRENAGO'.

BACKGROUND OF THE INVENTION

The present invention relates to a new and distinct cultivar of *Senecio* plant, botanically known as *Senecio cruentus*, and hereinafter referred to by the name 'Sene Nirenago'.

The new *Senecio* plant is a product of a planned breeding program conducted by the Inventor in Higashiomi, Shiga, Japan. The objective of the breeding program is to create new upright, uniformly mounding and vigorous *Senecio* plants with a freely-branching habit, early flowering and numerous attractive inflorescences.

The new *Senecio* plant originated from a cross-pollination conducted by the Inventor in March, 2016 of a proprietary selection of *Senecio cruentus* identified as code designation 16BonS-12-1, not patented, as the female, or seed, parent with a proprietary selection of *Senecio cruentus* identified as code designation 16BonS-12-2, not patented, as the male, or pollen, parent. The new *Senecio* plant was discovered and selected by the Inventor as a single flowering plant within the progeny of the stated cross-pollination in a controlled greenhouse environment in Higashiomi, Shiga, Japan in February, 2017.

Asexual reproduction of the new *Senecio* plant by terminal vegetative cuttings in a controlled greenhouse environment in Higashiomi, Shiga, Japan since October, 2018 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sene Nirenago'. These characteristics in combination distinguish 'Sene Nirenago' as a new and distinct *Senecio* plant:

1. Upright and uniformly mounded plant habit.
2. Vigorous growth habit.
3. Freely branching habit.
4. Freely flowering habit.
5. Daisy-type inflorescences with ray florets that are deep violet and light reddish purple in color.

Plants of the new *Senecio* can be compared to plants of the female parent selection. Plants of the new *Senecio* differ primarily from plants of the female parent selection in ray floret color as ray florets of plants of the new *Senecio* are deep violet and light reddish purple in color whereas ray florets of plants of the female parent selection are dark red in color. In addition, plants of the new *Senecio* have larger inflorescences than plants of the female parent selection.

Plants of the new *Senecio* can be compared to plants of the male parent selection. Plants of the new *Senecio* differ primarily from plants of the male parent selection in ray floret color as ray florets of plants of the new *Senecio* are deep violet and light reddish purple in color whereas ray florets of plants of the male parent selection are dark red in color. In addition, plants of the new *Senecio* are shorter than plants of the male parent selection.

Plants of the new *Senecio* can also be compared to plants of *Senecio cruentus* 'Sunsenegonana', disclosed in U.S. Plant Pat. No. 28,266. In side-by-side comparisons, plants of the new *Senecio* differ from plants of 'Sunsenegonana' in the following characteristics:

1. Plants of the new *Senecio* are shorter and broader than plants of 'Sunsenegonana'.

2. Plants of the new *Senecio* are more freely branching than plants of 'Sunsenegonana'.
3. Plants of the new *Senecio* have shorter, narrower and darker green-colored leaves than plants of 'Sunsenegonana'.
4. Plants of the new *Senecio* have smaller inflorescences than plants of 'Sunsenegonana'.
5. Inflorescences of plants of the new *Senecio* have more ray and disc florets than inflorescences than plants of 'Sunsenegonana'.
6. Plants of the new *Senecio* differ from plants of 'Sunsenegonana' in ray floret color as ray florets of plants of the new *Senecio* are deep violet and light reddish purple in color whereas ray florets of plants of 'Sunsenegonana' are dark violet and pink in color.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph at the top of the photographic sheet (FIG. 1) is a side perspective view of a typical flowering plant of 'Sene Nirenago' grown in a container.

Figure 2:
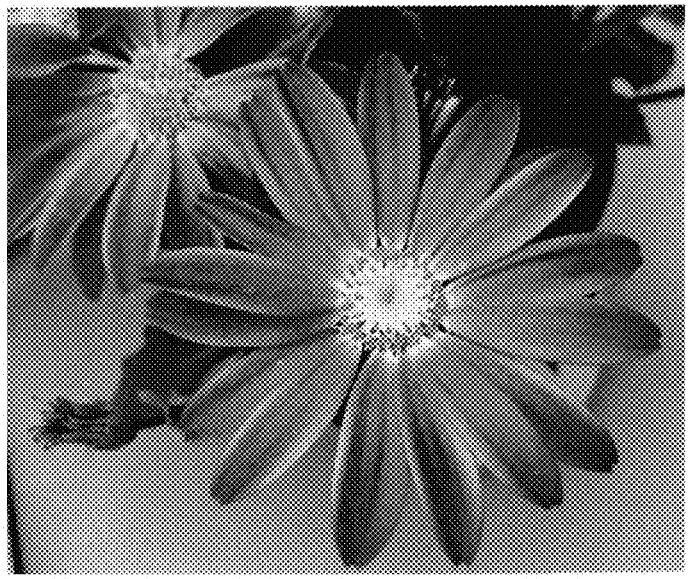

The photograph at the bottom of the photographic sheet (FIG. 2) is a close-up view of typical inflorescences of 'Sene Nirenago'.

DETAILED BOTANICAL DESCRIPTION

The aforementioned photographs, following observations and measurements describe plants grown during the late winter/early spring in 24-cm containers in an outdoor nursery in Higashiomi, Shiga, Japan and under cultural practices typical of commercial *Senecio* production. During the production of the plants, day temperatures averaged 10° C. and night temperatures averaged 5° C. Measurements and numerical values represent averages for typical flowering plants. Plants were six months old when the photographs and the detailed description were taken. In the following description, color references are made to The Royal Horticultural Society Colour Chart, 2015 Edition, except where general terms of ordinary dictionary significance are used.

Botanical classification: *Senecio cruentus* 'Sene Nirenago'.

Parentage:

*Female, or seed, parent.*—Proprietary selection of *Senecio cruentus* identified as code designation 16BonS-12-1, not patented.

*Male, or pollen, parent.*—Proprietary selection of *Senecio cruentus* identified as code designation 16BonS-12-2, not patented.

Propagation:

*Type.*—Terminal vegetative cuttings.

*Time to initiate roots, summer and winter.*—About one week at temperatures about 18° C. to 20° C.

*Time to produce a rooted young plant, summer and winter.*—About four weeks at temperatures about 18° C. to 20° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching.

Plant description:

*Plant form and growth habit.*—Upright and uniformly mounded plant habit; daisy-type inflorescences positioned above the foliar plane; vigorous growth habit; freely branching habit with about ten primary branches each with numerous secondary branches.

*Plant height.*—About 27.5 cm.

*Plant diameter.*—About 36.5 cm.

*Lateral branches.*—Length: About 19 cm. Diameter: About 2.3 mm. Internode length: About 2.6 cm. Strength: Strong. Aspect: Mostly upright to leaning outwardly. Texture: Sparsely pubescent. Color: Close to 137A.

*Leaf description.*—Arrangement: Alternate, simple. Length: About 3.8 cm. Width: About 3.9 cm. Shape: Cordate. Apex: Acute. Base: Cordate. Margin: Crenate to serrate; slightly undulate. Texture and luster, upper surface: Sparsely pubescent; matte. Texture and luster, lower surface: Moderately pubescent; rough; matte. Venation pattern: Pinnate; reticulate. Color: Developing and fully expanded leaves, upper surface: Close to NN137A; venation, close to NN137D. Developing and fully expanded leaves, lower surface: Close to NN137D; venation, close to NN138B. Leaf petioles: Length: About 2.8 cm. Diameter: About 2.2 mm. Texture, upper and lower surfaces: Smooth, glabrous. Color, upper and lower surfaces: Close to 138D.

Inflorescence description:

*Appearance.*—Daisy-type inflorescences with elliptic-shaped ray florets; inflorescences arising from upper leaf axils and positioned above the foliar plane on strong peduncles; disc and ray florets developing acropetally on a capitulum; inflorescences face mostly upright to slightly outwardly; freely flowering habit with about 76 inflorescences developing per plant during the flowering season.

*Fragrance.*—None detected.

*Natural flowering season.*—Plants of the new *Senecio* begin flowering about 22 weeks after planting; plants flower continuously from winter to late spring in Japan; inflorescences persistent.

*Inflorescence buds.*—Height: About 1.4 cm. Diameter: About 6.5 mm. Shape: Globose. Color: Close to N88A.

*Inflorescence size.*—Diameter: About 5 cm. Depth (height): About 1.5 cm. Disc diameter: About 1 cm.

*Receptacles.*—Diameter: About 5.9 mm. Height: About 1.6 mm. Color: Close to 144B.

*Ray florets.*—Quantity and arrangement: About 20 per inflorescence arranged in a single whorl. Length: About 2.3 cm. Width: About 7 mm. Shape: Elliptic. Apex: Acute. Base: Attenuate. Margin: Entire, not undulate. Aspect: Initially upright, then horizontal; flat. Texture, upper and lower surfaces: Smooth, glabrous. Color: When opening, upper surface: Close to N88A; towards the base, close to N80A. When opening, lower surface: Close to 91D. Fully opened, upper surface: Close to N89D; towards the base, close to N75A; venation, close to N89D and N75A; colors do not change with subsequent development. Fully opened, lower surface: Close to 76C; venation, close to 76C; color does not change with subsequent development.

*Disc florets.*—Quantity per inflorescence: About 119. Length: About 7.5 mm. Diameter, at apex: About 1.6 mm. Diameter, at base: About 0.7 mm. Shape: Tubular; apex dentate, five-pointed. Texture: Smooth, glabrous. Color, immature: Close to 8B. Color, mature: Close to 8D.

*Phyllaries.*—Quantity and arrangement: About 15 per inflorescence arranged in a single whorl. Length: About 1.5 mm. Width: About 1.3 mm. Shape: Lanceolate; moderately recurved. Apex: Narrowly acute. Base: Fused. Margin: Entire. Texture, upper and lower surfaces: Smooth, glabrous. Color, upper surface: Close to 143C. Color, lower surface: Close to 143A.

*Peduncles.*—Length: About 3.1 cm. Diameter: About 1.4 mm. Strength: Strong. Aspect: Mostly upright to outwardly. Texture: Smooth, glabrous. Color: Close to 137A.

*Reproductive organs.*—Androecium: Present on disc florets only. Filament length: About 3.1 mm. Filament color: Close to 145D. Anther size: About 1 mm by 1.5 mm. Anther shape: Narrowly ellipsoidal. Anther color: Close to 15B. Pollen amount: Moderate. Pollen color: Close to 15B. Gynoecium: Present on both ray and disc florets. Pistil length: About 6.1 mm. Stigma shape: Bi-parted. Stigma color: Close to 150B. Style color: Close to 145C. Ovary color: Close to 145C.

*Seeds and fruits.*—To date, seed and fruit development have not been observed on plants of the new *Senecio*.

Pathogen & pest resistance: To date, plants of the new *Senecio* have not been observed to be resistant to pathogens and pests common to *Senecio* plants.

Temperature tolerance: Plants of the new *Senecio* have been observed to tolerate temperatures ranging from about 0° C. to about 30° C.

It is claimed:

1. A new and distinct *Senecio* plant named 'Sene Nirenago' as illustrated and described.

* * * * *